(12) United States Patent
Seippel

(10) Patent No.: US 9,776,771 B2
(45) Date of Patent: Oct. 3, 2017

(54) SCREW CAP LIDDED CONTAINER

(71) Applicant: Eppendorf AG, Hamburg (DE)

(72) Inventor: Martin Seippel, Ammersbek (DE)

(73) Assignee: Eppendorf AG, Hamburg (DE)

( * ) Notice: Subject to any disclaimer, the term of this patent is extended or adjusted under 35 U.S.C. 154(b) by 0 days.

(21) Appl. No.: 14/553,021

(22) Filed: Nov. 25, 2014

(65) Prior Publication Data

US 2016/0001931 A1 Jan. 7, 2016

(30) Foreign Application Priority Data

Nov. 26, 2013 (EP) .................................... 13194408

(51) Int. Cl.
| | |
|---|---|
| *C12M 1/00* | (2006.01) |
| *B01L 1/00* | (2006.01) |
| *B65D 41/04* | (2006.01) |
| *B01L 3/08* | (2006.01) |
| *C12M 1/24* | (2006.01) |
| *B65D 1/02* | (2006.01) |
| *B65D 51/16* | (2006.01) |
| *C12M 3/00* | (2006.01) |

(52) U.S. Cl.
CPC ............ *B65D 41/0471* (2013.01); *B01L 3/08* (2013.01); *B65D 1/0207* (2013.01); *B65D 41/0414* (2013.01); *B65D 51/1672* (2013.01); *C12M 23/02* (2013.01); *C12M 23/08* (2013.01); *C12M 23/38* (2013.01); *C12M 23/46* (2013.01); *C12M 29/20* (2013.01); *B01L 2300/048* (2013.01)

(58) Field of Classification Search
CPC ...... C12M 23/08; C12M 23/24; C12M 23/36; C12M 23/38; B01L 3/14
See application file for complete search history.

(56) References Cited

U.S. PATENT DOCUMENTS

| | | | |
|---|---|---|---|
| 1,902,754 A | 3/1933 | Bechler | |
| 3,612,324 A * | 10/1971 | Malick | .................. B65D 41/06 215/222 |
| 4,289,248 A | 9/1981 | Lynn | |
| 4,546,085 A | 10/1985 | Johansson et al. | |

(Continued)

FOREIGN PATENT DOCUMENTS

| | | |
|---|---|---|
| AT | 304290 | 12/1972 |
| CN | 102941962 A | 2/2013 |

(Continued)

*Primary Examiner* — Nathan Bowers
(74) *Attorney, Agent, or Firm* — Vidas, Arrett & Steinkraus, P.A.

(57) ABSTRACT

A screw cap lidded container for laboratory use includes a container body defining a chamber, a tubular section of the container body that is connected at the rear to the chamber and has a container opening in the front and an external thread on the outer periphery of the tubular section. There is a circumferential first sealing surface on the tubular section and at least one first projection, which projects from the container body at a peripheral position of the tubular section, and a screw cap having an internal thread on the inner periphery that can be screwed onto the external thread with thread play, a second sealing surface on the screw cap can be brought into sealing contact with the first sealing surface, and at least one second projection, which projects at a peripheral position of the screw cap.

16 Claims, 12 Drawing Sheets

(56) References Cited

U.S. PATENT DOCUMENTS

| | | | |
|---|---|---|---|
| 5,038,967 A | 8/1991 | Braun | |
| 5,395,006 A | 3/1995 | Verma | |
| 5,398,837 A | 3/1995 | Degrassi | |
| 5,462,186 A | 10/1995 | Ladina et al. | |
| 5,565,353 A | 10/1996 | Klebe et al. | |
| 5,578,491 A | 11/1996 | Kayal et al. | |
| 6,085,922 A | 7/2000 | Esser | |
| 6,114,165 A | 9/2000 | Cai et al. | |
| 7,523,839 B2 * | 4/2009 | Savicki | B65D 43/0231 220/303 |
| 2009/0218306 A1 | 9/2009 | Menchel et al. | |

FOREIGN PATENT DOCUMENTS

| | | |
|---|---|---|
| CN | 203112846 U | 8/2013 |
| DE | 2346074 | 3/1975 |
| DE | 4340229 | 10/1995 |
| EP | 0117722 | 9/1984 |
| EP | 0791649 | 7/2002 |
| FR | 2597440 | 10/1987 |
| GB | 2035972 | 6/1980 |
| GB | 2288390 | 10/1995 |
| WO | 97/31833 | 9/1997 |
| WO | 2007/071287 | 6/2007 |

\* cited by examiner

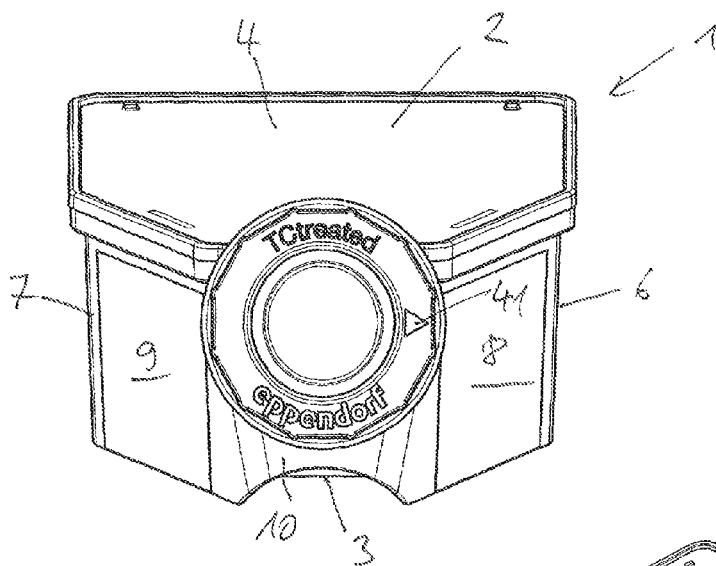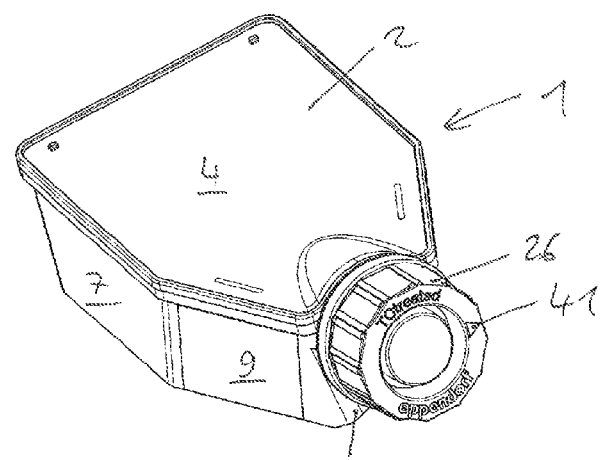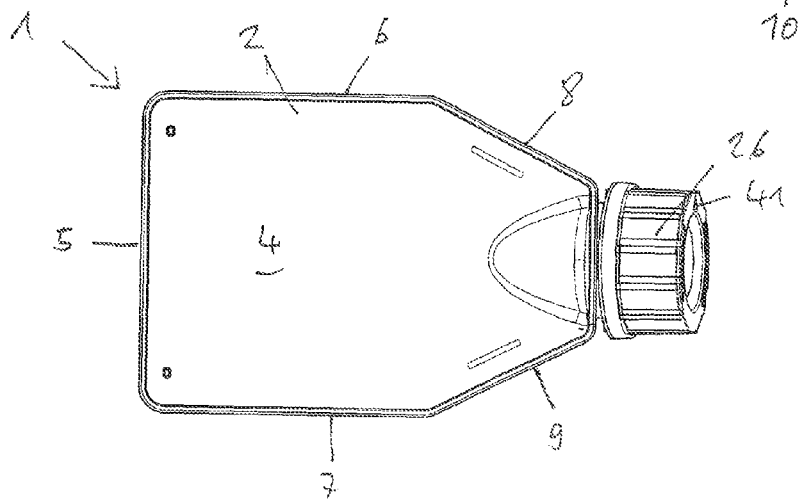

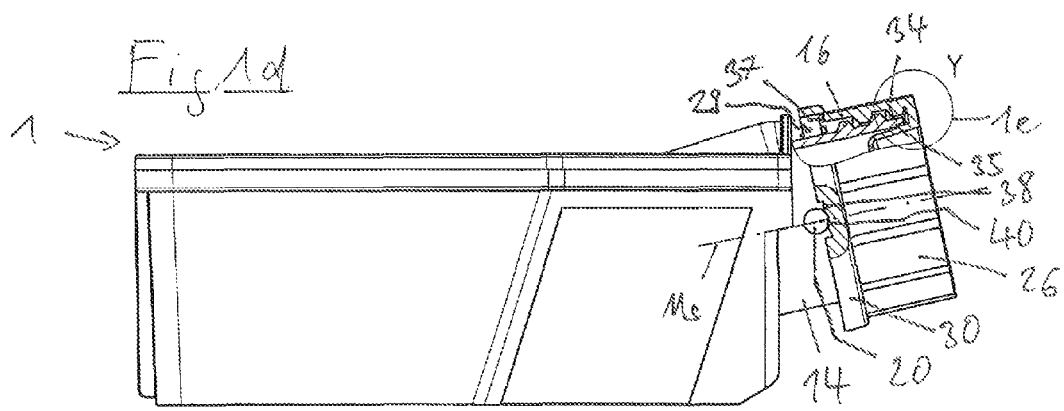
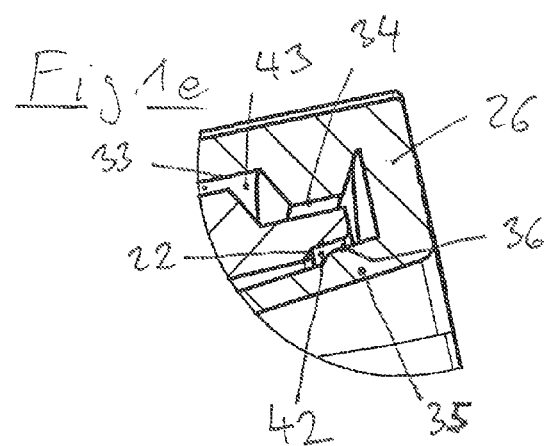

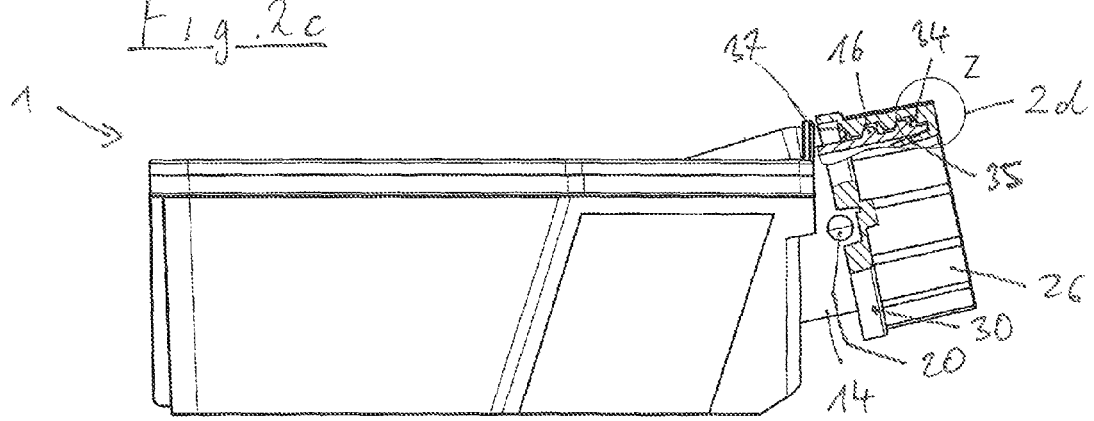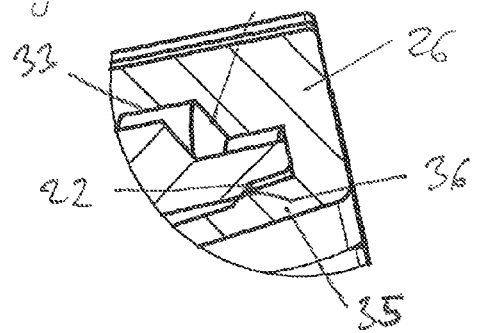

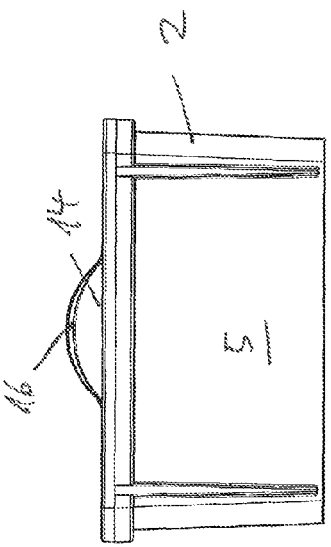
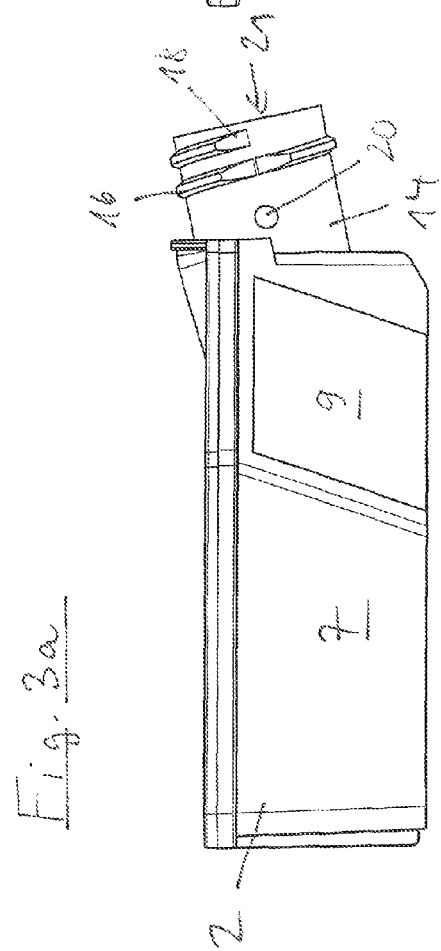
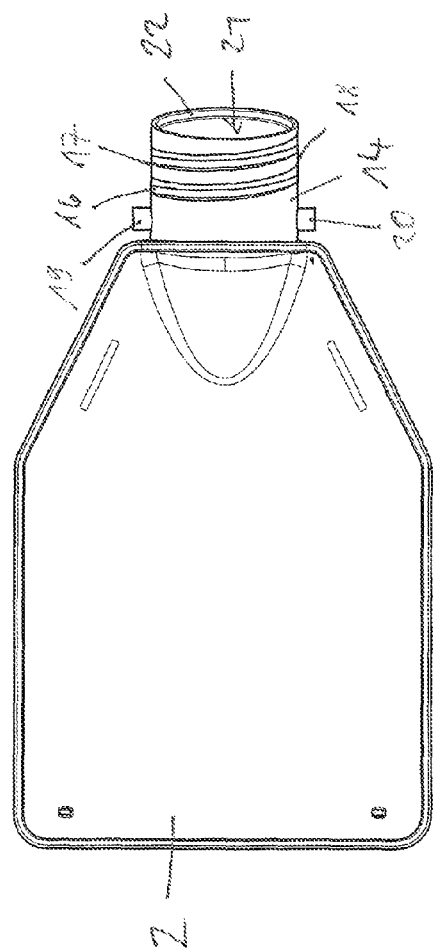

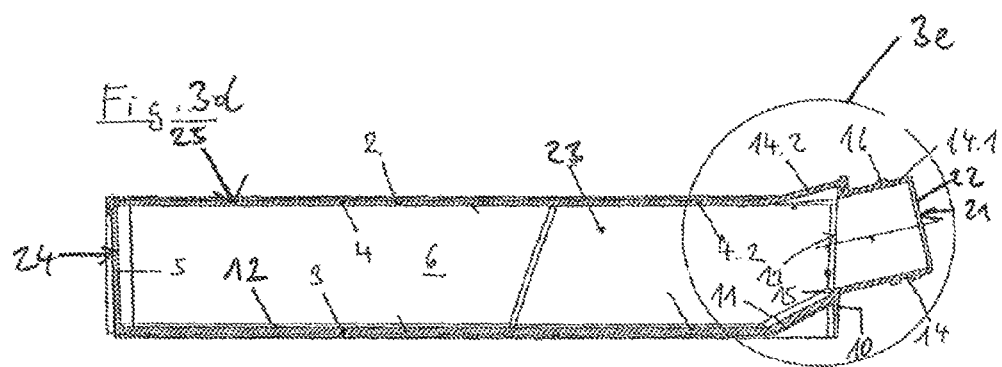
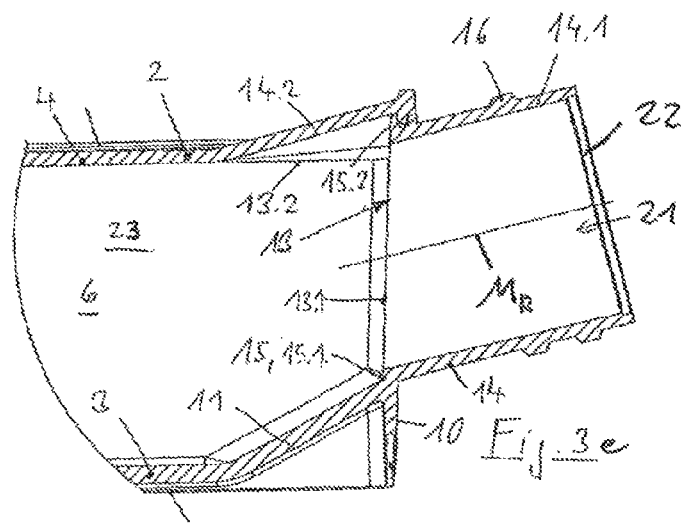

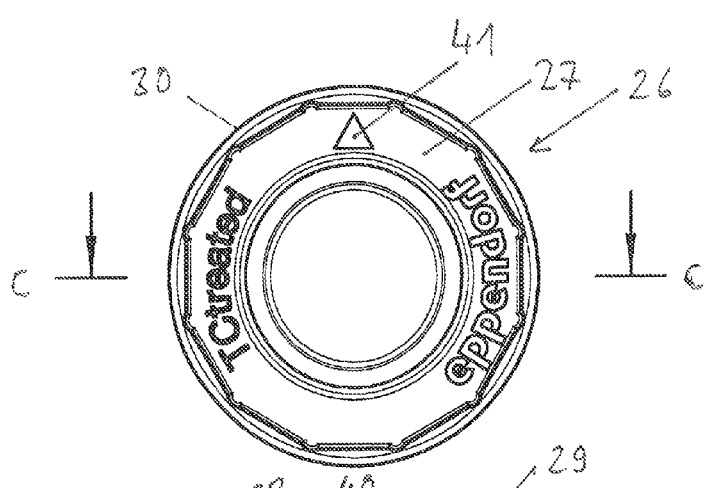
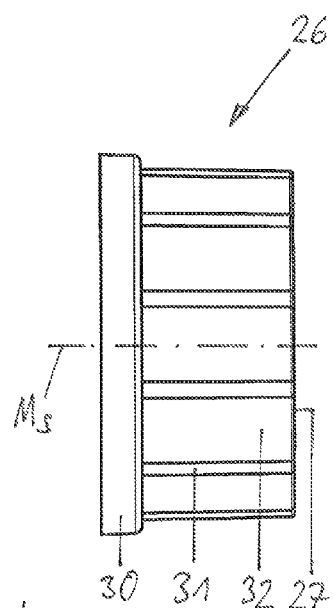
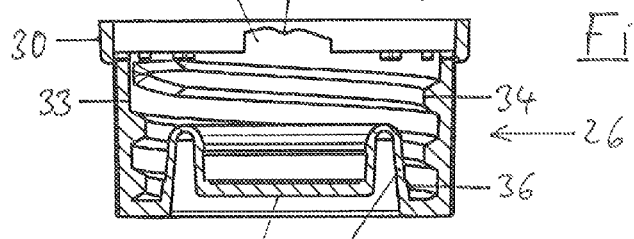
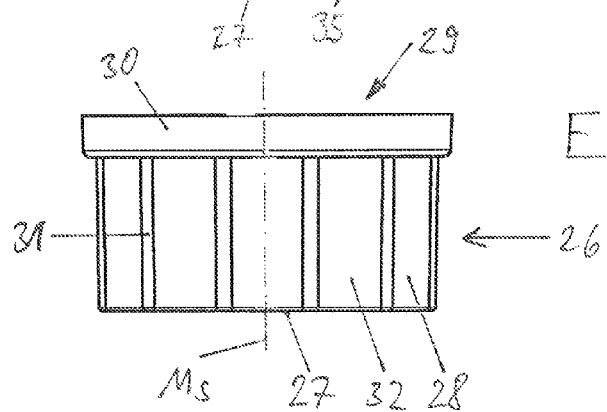

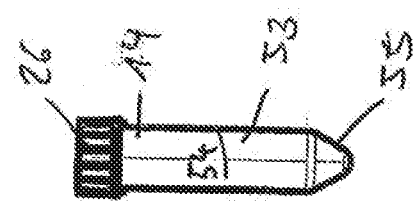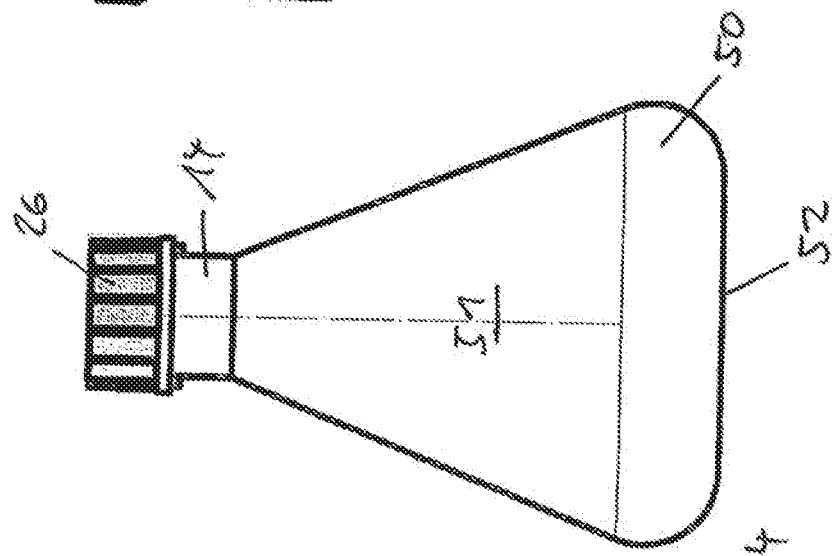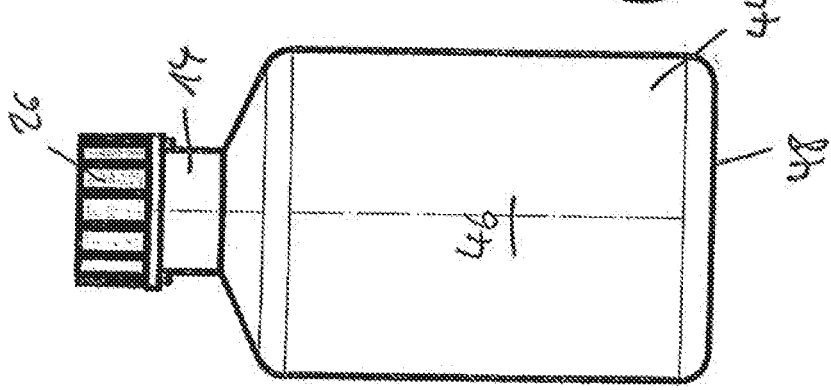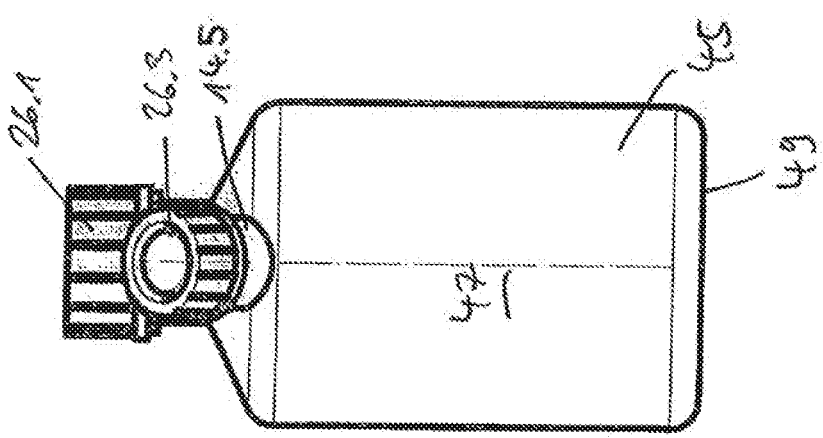

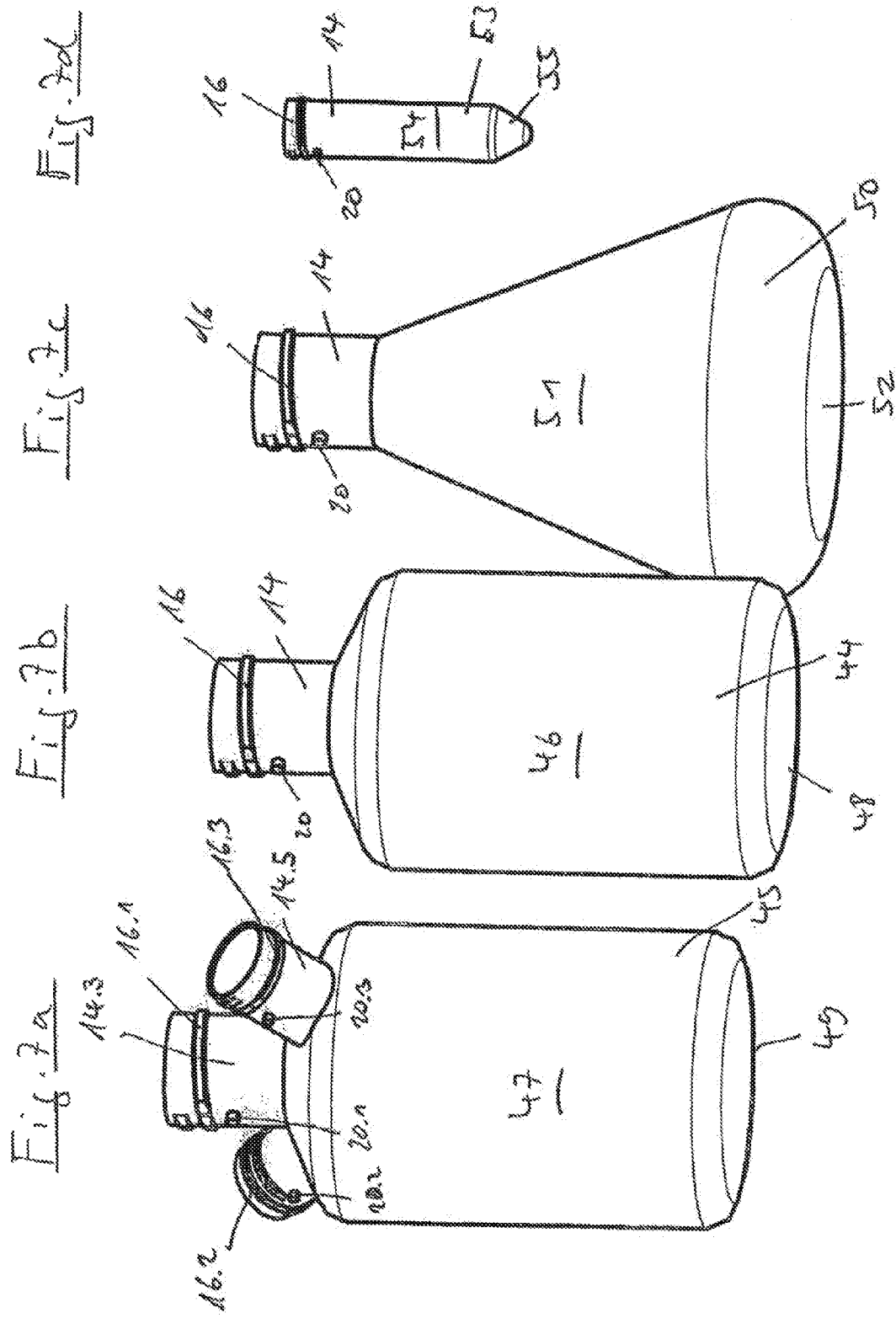

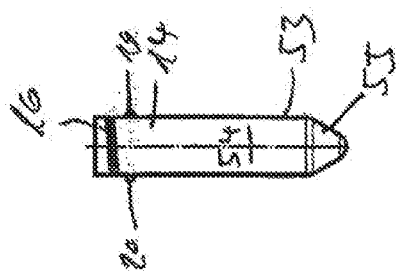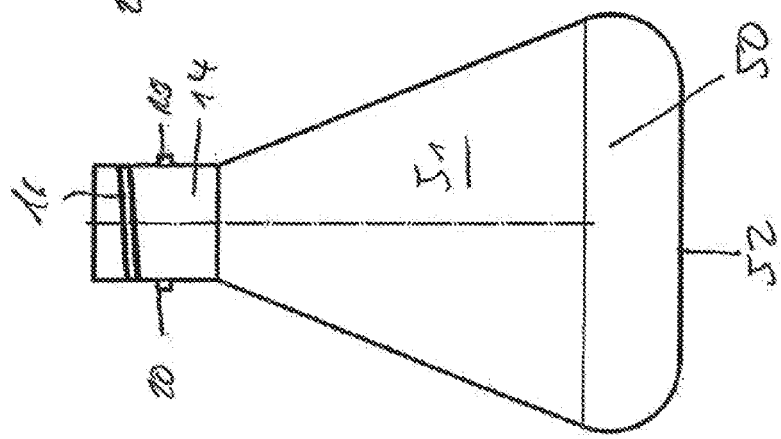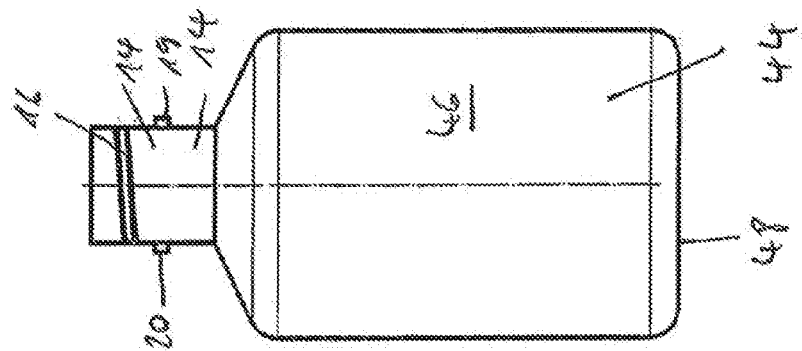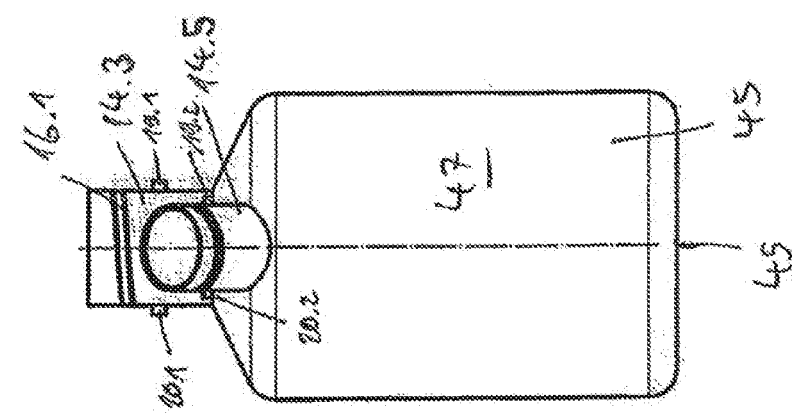

SCREW CAP LIDDED CONTAINER

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The invention relates to a screw cap lidded container for laboratory use. The invention relates particularly to a screw cap lidded container for use in biological, microbiological, medical, chemical or pharmaceutical laboratories.

The screw cap lidded container is, for example, a culture flask or another culture container for cultivating cells, tissue or microorganisms, or a laboratory bottle or another laboratory container for storing liquids and other media.

Culture containers are used in the laboratory for cultivating and harvesting cells, tissues or microorganisms. They have a container body in which there is a culture chamber that is accessible through a container opening. The containers have a screw cap for sealed closure of the container opening. The screw cap can be loosened somewhat for gassing the media in the culture chamber, e.g., using $CO_2$ in the incubator. Here, it cannot be guaranteed that a sufficient, reproducible ventilation cross-section is attained. In addition, the screw cap can loosen completely due to vibrations of the incubator, and fall off.

Further, culture flasks are known that have a membrane filter in a screw cap in order to permit an exchange of gas between the interior of the flask and the surrounding area when the screw cap is screwed on. These culture flasks have the disadvantage that liquid can escape, particularly when the cell culture flask is tipped so that liquid is in contact with the membrane or the filter.

Cell culture flasks having a screw cap which engages into a defined ventilation setting in which the screw cap is not completely sealed, are also known. By further screwing on the screw cap beyond the ventilation setting, the screw cap can be brought into the sealed setting in which the cell culture flask is sealed gas-tight and liquid-tight. For locking in the ventilation setting, the cell culture flask has a plurality of lobes on the neck of the flask and corresponding axially aligned grooves on the inner periphery of the screw cap. When tightening the cap, the lobes, after overcoming light resistance, engage in the grooves before the screw cap closes the container opening. The interior of the flask is ventilated in this locked setting. With further rotation of the screw cap, again against light resistance, the lobes leave the grooves and the screw cap seals the cell culture flask. The ventilation of this culture flask is insufficient for some applications.

Given this background, an object of the invention is to create a screw cap lidded container with which sufficient ventilation is more reliably attained.

The screw cap lidded container according to the invention for laboratory use comprises
 a container body defining a chamber,
 a tubular section of the container body that is connected at the rear to the chamber and has a container opening in the front,
 an external thread on the outer periphery of the tubular section,
 a circumferential first sealing surface on the tubular section,
 at least one first projection, which projects from the container body at a peripheral position of the tubular section,
 a screw cap,
 an internal thread on the inner periphery of the screw cap that can be screwed onto the external thread with thread play,
 a circumferential second sealing surface on the screw cap, that by screwing the screw cap tightly onto the tubular section can be brought into sealing contact with the first sealing surface, and
 at least one second projection, which projects from the screw cap at a peripheral position,
 wherein the first projection on the front side, in a circular cylindrical cut surface about the central axis of the tubular section, has an increasing shoulder, and/or the second projection on the back side, in a circular cylindrical cut surface about the central axis of the screw cap, has an increasing shoulder, wherein when screwing the screw cap tightly onto the tubular section, the first and second projections come into contact and glide onto each other with the at least one increasing shoulder, whereby a forward directed force is exerted on the screw cap, through which, in a ventilation setting in which a ventilation gap is present between the first and second sealing surfaces, the internal thread is pressed with a thread flank against a thread flank of the external thread, the first and second projections are moved past each other during further screwing tightly and the first and second sealing surfaces attain a sealed setting in which they lie sealed against each other.

BRIEF SUMMARY OF THE INVENTION

In the present application, the specifications "front" and "back" refer to a screw cap lidded container that has the screw cap closest to the viewer so that from the viewer's point of view the bottom of the cap is arranged in front and the internal thread is further behind, and the container opening is arranged in front and the external thread is further behind.

The invention is based on the recognition that with known cell culture flasks the locking in the ventilation setting is precise only in the peripheral direction of the flask neck. The locking occurs here only in the rotation direction of the cap. In contrast, in the axial direction of flask neck, a displacement of the screw cap on the flask neck is possible even in the ventilation setting due to the thread play. Due to this displacement, the seal of the screw cap takes on different positions with respect to the flask opening such that the ventilation cross-section varies. It is even possible, that by pressing on the screw cap the seal is sealed to some extent. As a consequence, the ventilation cross-section is not precisely reproducible and the ventilation cross-section can be insufficient. A further disadvantage is the poor demoldability of the grooves which are produced by injection molding the screw cap. For this, a threaded core with appropriate projections is used that deforms the grooves strongly during cutting. The precision of the grooves in the peripheral direction is also impacted by this.

According to the invention, a precise positioning in the axial direction of the screw cap in the ventilation setting is attained due to the first and second projections, which rest against each other in the ventilation setting such that the internal thread is pressed with a thread flank against a thread flank of the external thread. Due to this, the thread play in the ventilation setting is eliminated. As the thread play in the axial direction is eliminated, the user is assured that the ventilation gap between the first and second sealing surfaces is always reproduced precisely. Thus, the ventilation setting always attains the constructively specified ventilation cross-section. Sufficient and reproducible ventilation is thereby guaranteed. Starting from the ventilation setting, the screw cap can be further screwed tightly wherein the first and second projections are moved past each other. The sealed setting is attained by further tightly screwing the screw cap in that the first and second sealing surfaces lie sealed on each other. In the sealed setting the screw cap lidded container is sealed gas-tight and liquid-tight.

The thread play is desired in order to smoothly screw the screw cap onto the tubular section at least up to the contact of the first and second projections. In addition, due to the thread play in the ventilation setting a spiral-shaped circumferential ventilation channel is set between the external and internal thread, by means of which the ventilation cross-section is connected between the sealing surface and the surrounding area. The axial thread play is preferably 0.5-1 mm. Through this, a ventilation cross-section results that is preferably 6-8 mm$^2$, whereby however a cross-section of up to 40 mm$^2$ can also be realized.

According to one design, the tubular section has the first sealing surface on the inner periphery of the tubular section, and the screw cap has the second sealing surface on a stopper projecting from the cap bottom. Due to this, a particularly tight lock can be attained for liquids and gases. Preferably the first sealing surface is arranged on the inner periphery of the container opening. It is however also possible to arrange the first sealing surface in the tubular section at a distance from the container opening. Further, the first sealing surface can be present on the face side or on the outer periphery of the tubular section, preferably between the external thread and the face surface. Further, the first sealing surface can extend beyond a plurality of the named regions.

According to a preferred design, the at least one first projection has on the front side a decreasing shoulder in the circular cylindrical cut surface about the central axis of the tubular section, and/or the at least one second projection has on the back side a decreasing shoulder in the circular cylindrical cut surface about the central axis of the screw cap, so that during further screwing the screw cap tightly from the ventilation position into the sealed position the first and second projections glide over one another with the at least one decreasing shoulder, whereby the forward directed force exerted onto the screw cap is completely or partially absorbed until the sealed setting is attained. With this design, the thread play is again completely or partially effective when the screw cap is rotated from the ventilation setting into the sealed setting. This facilitates screwing the screw cap tightly up to attaining the sealed setting. Additionally, this favors a centering of the first sealing surface on the second sealing surface which is advantageous for sealing. Finally, this design facilitates the user's recognition of attaining the ventilation setting and the sealed setting, because the screwing torque noticeably decreases and then increases again during screwing from the ventilation setting into the sealed setting, or vice versa. Alternatively, the projections are created such that the thread play is eliminated over the entire displacement distance from the ventilation setting up to the sealed setting.

According to further design, the container body has a plurality of first projections distributed uniformly about the tubular section, and the screw cap has a corresponding number of second projections distributed uniformly about the cap opening. Due to the uniform distribution of the first and second projections, a uniform transfer of the contact pressure in the ventilation setting and the maintaining of the desired ventilation cross-section is further supported.

According to a preferred design, the container body has two first projections arranged on diametrically opposed sides of the tubular section, and the screw cap has two second projections arranged on diametrically opposed sides of the cap opening. This design particularly has the production advantage that the first projection can be arranged in the plane of separation of an injection mold. Due to this, the use of comparatively simple injection molds is facilitated.

Preferably the at least one first projection and the at least one second projection have an increasing shoulder. This favors a gradual increase of the force acting on the screw cap up to attaining the ventilation setting. Alternatively, only the at least one first projection or the at least one second projection has an increasing shoulder. Preferably the at least one first projection and the at least one second projection have a decreasing shoulder. Due to this, a gradual increase of the force acting on the screw cap is attained during rotating the screw cap back from the sealed setting into the ventilation setting. Alternatively, only the at least one first projection or the at least one second projection has a decreasing shoulder.

According to a further design, the at least one first projection is convex on the front side and/or the at least one second projection is convex on the back side. This favors a gentle sensitive increase in force that can be applied, up to attaining the ventilation setting. Preferably the curvature of the first projection and/or the second projection extends in each case across the increasing shoulder and the decreasing shoulder. Alternatively only the increasing shoulder and/or only the decreasing shoulder is convex. According to another design, the increasing shoulder of the first projection and/or the second projection is a chamfer and/or the decreasing shoulder of the first projection and/or the second projection is a chamfer.

According to another design, the at least one first projection projects outwards behind the external thread of the tubular section and/or the at least one second projection projects behind the internal thread of the cap casing. These designs are advantageous for injection molding the culture container from plastic.

According to a further design, the at least one first projection is a pin projecting radially from the tubular section. According to a preferred design the pin is circular cylindrical. This design saves material and is easy to manufacture.

According to a further design, the at least one second projection is a hump projecting from the cap casing behind the internal thread. Preferably the width of the hump is greater than the diameter of the pin so that the first projection in the ventilation setting is positioned securely on the outer end of the hump.

According to a preferred design, the at least one second projection on the outer end has a latching groove into which the at least one first projection latches in the ventilation setting. According to an alternative design, the at least one first projection on the outer end has a latching groove into which the at least one second projection latches in the ventilation setting. Due to this, the screw cap is secured in the ventilation setting. Preferably the latching groove is formed on the outer end of the curvature of a hump, and a circular cylindrical pin latches into the latching groove.

According to a further design, the latching groove is rounded in order to facilitate the targeted rotation of the first or second projection out of the latching groove. The latching groove is preferably rounded on the two lateral transitions to the outer end of the first or second projection and/or to the base thereof. Alternatively the two groove flanks of the latching groove are chamfered.

According to a further design, the at least one second projection projects inward from the cap casing. This design avoids user contact with the first and second projection, which can lead, for example, to damaging the protective gloves.

According to a further design, the screw cap on the outer edge of the cap casing thereof has a radial widening, and the at least one second projection is arranged within the widening. The widening favors a targeted housing of the second and the first projections, and a secure grip and screwing on of the screw cap.

According to a further design, the external thread and/or the internal thread have at least one flattening of the thread profile. The flattening has production advantages, if during injection molding they are arranged in the plane of separation of a tool. Additionally, the gas exchange can also occur past the flattening. The thread profile in the region of the flattening is preferably flattened up to the circular cylindrical periphery of the tubular section.

According to a further design, the screw cap on the outside has a marking whose alignment indicates the ventilation setting and/or the sealed setting. With a culture flask or another culture container, that during cultivation has a specific preferred setting, the alignment of the marking in the ventilation setting or in the sealed setting relates preferably to the position of the culture container in the preferred setting. For example, the ventilation setting is indicated by the alignment of the marking at 3 o'clock in the preferred setting. According to a further design, at least one further marking is arranged on the container body which is aligned to the marking on the screw cap in the ventilation setting and/or in the sealed setting.

According to a further design, the screw cap lidded container is a culture flask, or a test tube, or a roller bottle or a spinner bottle or an Erlenmeyer flask or a laboratory bottle.

A culture flask has a flat, substantially rectangular flask body, having bottom, cover and side walls which define a chamber (culture chamber). A flask neck projects outward from a narrow front side wall. The flask neck has the external thread and can be sealed by the screw cap. Culture flasks serve particularly for propagating adherent cells which accumulate on the surface of the bottom wall. The surface of the bottom wall is called the growth area. The four popular flask sizes are generally called T-25, T-75, T-175 and T-300, wherein each number respectively specifies the effective growth area in $cm^2$. Other formats are also offered on the market either with smaller growth areas (e.g., 12 $cm^2$) or a multiple of the standard areas stated above (e.g., multi-layer flasks). Culture flasks are also used for the cell proliferation of suspended cells, which have no or nearly no adhesion to the surface.

Roller bottles are round bottles having a bottle neck, which can be closed using a screw cap. They have effective growth areas from 700 to 2,000 $cm^2$ and are therefore particularly suited for the mass cultivation of adherent cells. Roller bottles during the cultivation are rotated about the longitudinal axis thereof in a special apparatus.

Spinner bottles are round bottles having a large volume with a wide central bottle neck for introduction of an agitator which is held sealingly by a screw cap in the wide bottle neck. At least one (preferably two) less wide bottle neck is arranged on the side of the central bottle neck that serves for the introduction and removal of media and is sealed by means of a screw cap. Spinner bottles can be used alternatively to roller bottles for mass cultivation of suspended cells, or also of adherent cells. In the case of a mass cultivation of adherent cells, for enlarging the effective growth area, a carrier material that is held constantly in suspension by an agitator and upon which the cells can grow, can be introduced into the growth media. Thus, effective growth areas of 700 to 18,000 $cm^2$ per gram of carrier material can be attained.

Further details for the implementation and application of culture flasks, roller bottles, and spinner bottles are described in "Cell and Tissue Culture" by Lindl and Gstraunthaler, Spektrum Akademischer Verlag, Heidelberg 2008, 6th Edition, pages 71 to 72, 323 to 325, 330 to 332. The invention relates to all known designs and uses of culture flasks, roller bottles and spinner bottles.

Test tubes and conical tubes are simply cylindrical containers that are conical or ball-shaped at the lower end, which at the upper end have a tubular section with external thread upon which the screw cap is screwed. Test tubes can be used for cultivating suspension cells and spheroid cells, for cultivating aerobic bacteria, yeasts, and other microorganisms, and for storing components and liquids.

In the scope of mass cultivation of cells, the cited container types or at least a part thereof are used sequentially in the following order: test tubes, cell culture flasks, roller bottles and spinner bottles.

Erlenmeyer flasks can be used for cultivating suspension cells and spheroid cells, adherent cells, and for cultivating aerobic bacteria, yeasts and other microorganisms.

Laboratory flasks are used in the laboratory for the storing liquids, for example.

With a laboratory bottle or another laboratory container, the screw cap can, before loosening from the container body, be brought initially into the ventilation setting, in order to gradually discharge vapors, which would exit abruptly if the screw cap were immediately loosened from the container body. This can be particularly advantageous if the laboratory bottle is filled with a liquid with high vapor pressure, or respectively with a liquid which releases aggressive or health endangering vapors.

According to a further design, the container body is produced from polystyrene or from polycarbonate or another plastic. These materials are advantageous particularly for the adhesion of cells, and with respect to the high transparency thereof. The screw cap, according to a further design, is produced from polypropylene or polyethylene or from polytetrafluoroethylene or from another plastic or from a combination of the named materials.

BRIEF DESCRIPTION OF THE SEVERAL VIEWS OF THE DRAWINGS

The invention will be further explained with reference to the accompanying drawings of exemplary embodiments. The drawings show:

FIG. 1a shows a culture flask with a lid in a ventilation position in a front view, FIG. 1b is a perspective view at an angle from the front and from the left side, FIG. 1c is a top view of the culture flask of FIG. 1a, FIG. 1d shows a partially cut side view from the left side of the culture flask, FIG. 1e shows an enlarged detail 1e from FIG. 1d;

FIG. 2c is a partially cut side view from the left side and FIG. 2d is an enlarged detail 2d from FIG. 2c;

FIG. 3a shows the container body of the same culture flask in a side view from the left side, FIG. 3b is a top view of the container body, FIG. 3c is a rear view of the container body, FIG. 3d is a longitudinal section and FIG. 3e is an enlarged detail from FIG. 3d;

FIG. 4a shows the screw cap of the same culture flask in a front view,

FIG. 4b is a top view,

FIG. 4c shows a section along the line c-c from FIG. 4a,

FIG. 4d is a side view, and

FIG. 6a shows the spinner bottle,

FIG. 6b shows a roller bottle,

FIG. 6c shows an Erlenmeyer flask and

FIG. 6d shows a test tube, respectively in a side view;

FIG. 7a shows the container body of spinner bottle,

FIG. 7b shows a roller bottle,

FIG. 7c shows an Erlenmeyer flask and

FIG. 7d shows a test tube, respectively in a perspective view from below and from the side; and FIG. 8a shows the container body of spinner bottle, FIG. 8b shows the roller bottle, FIG. 8c shows an Erlenmeyer flask and FIG. 8d shows a test tube, respectively in a side view.

DETAILED DESCRIPTION OF THE INVENTION

Figure 2A:
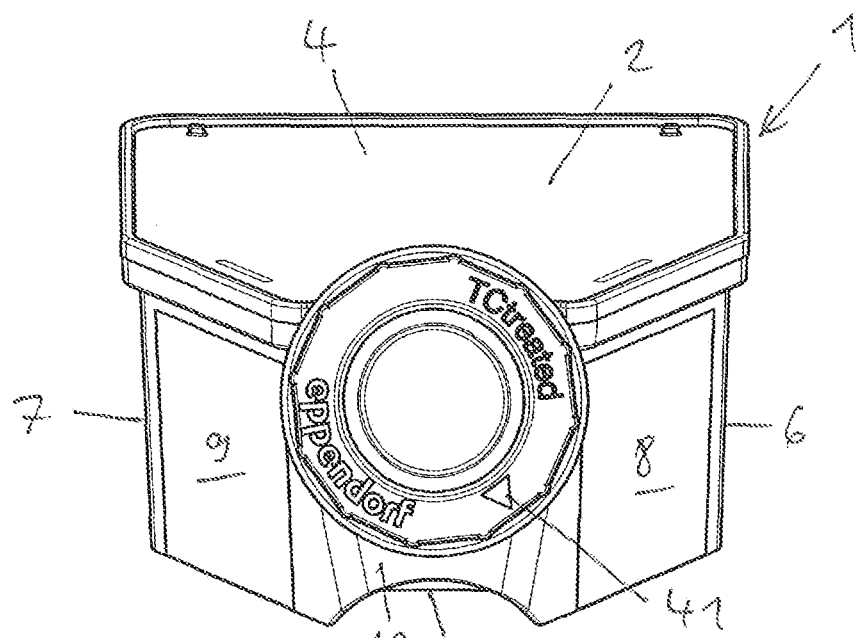
FIG. 2a shows the culture flask with the screw cap in the sealed setting in a front view.
Figure 2B:
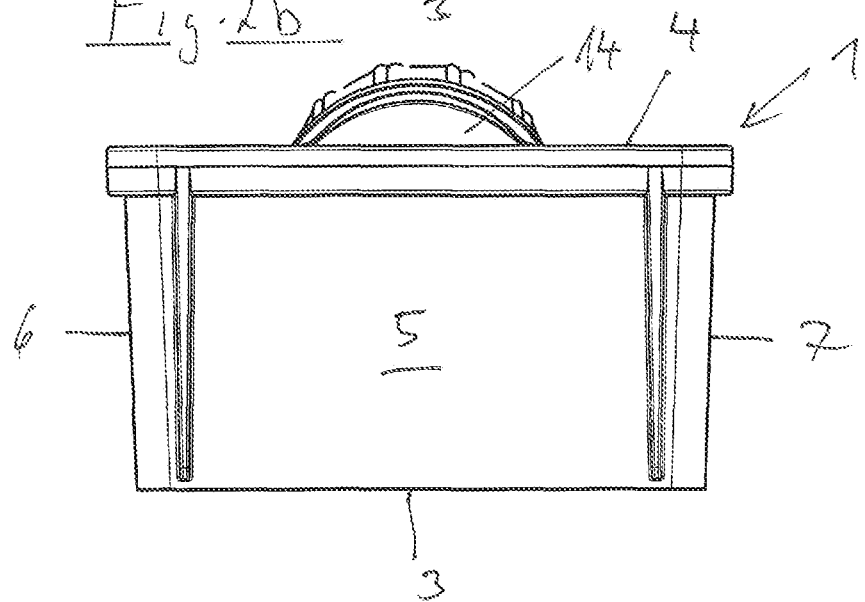
FIG. 2b is a rear view.
Figure 4E:
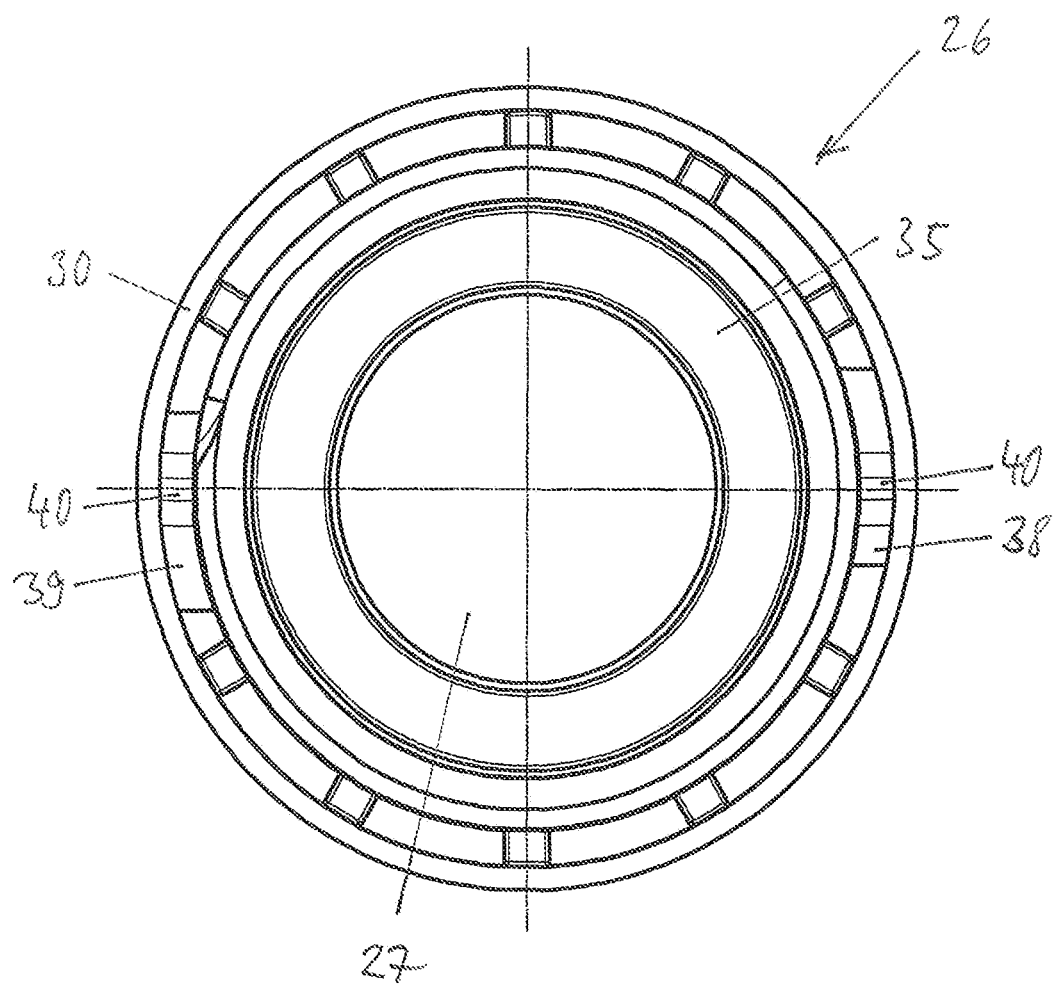
FIG. 4e is a rear view.
Figure 5A:
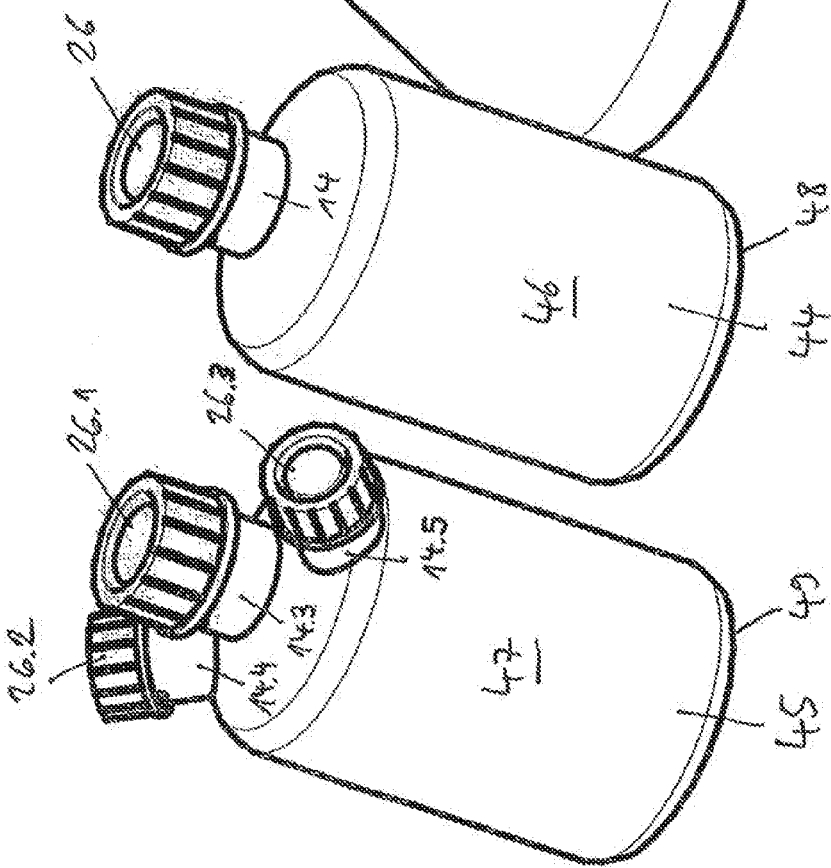
FIG. 5a shows a spinner bottle.
Figure 5B:
FIG. 5b shows a roller bottle (FIG. 5b)
Figure 5C:
FIG. 5c shows an Erlenmeyer flask.
Figure 5D:
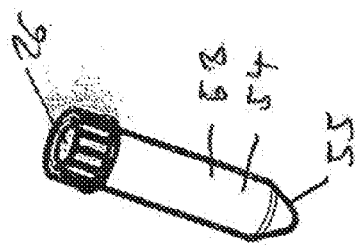
FIG. 5d shows a test tube, respectively in a perspective view from above and from the side.

While this invention may be embodied in many different forms, there are described in detail herein a specific preferred embodiment of the invention. This description is an exemplification of the principles of the invention and is not intended to limit the invention to the particular embodiment illustrated.

In the following, the specifications "top", "above", "bottom", and "below" relate to the arrangement of a culture flask with the bottom wall on a horizontal level surface and the cover wall above the bottom wall.

According to FIGS. 1a-1e, 2a-2d and 3a-3d, a culture container 1 according to the invention (called "culture flask" in the following) has a container body 2 (called "flask body" in the following) with a substantially planar bottom wall 3, and a substantially planar cover wall 4, which are aligned parallel to each other. The bottom wall 3 and the cover wall 4 each have a substantially rectangular section in the rear, and a substantially trapezoidal section in the front.

The distance region between the bottom wall 3 and the cover wall 4 is bridged by side walls 5, 6, 7, 8, 9, 10, which are connected to the edges of the bottom wall 3 and the cover wall 4.

The front edge of the trapezoidal section of the bottom wall is connected to a trapezoidal slanted wall 11. The front edge of the slanted wall 11 ends a short distance behind the front edge of the cover wall 4. The front side wall 10 is arranged between this edge of the slanted wall 11 and the front edge of the cover wall 4. The front side wall 10 extends below the front edge of the slanted wall 11 to the level of the lower side of the bottom wall 3 (see FIGS. 3d and 3e).

The front longitudinal side walls 8, 9 also bridge the distance between longitudinal edges of the slanted wall 11 and the front longitudinal edges of the cover wall 4.

The top of the bottom wall is a planar growth area 12.

An opening 13 is present in a region of the front side wall 10 bordering the cover wall 4, and in the bordering region of the cover wall 4. A lower opening section 13.1 of the opening 13, which is arranged in the front side wall 10, is arranged above the slanted wall 11. Thus the opening 13 is disposed at a distance in the vertical direction from the bottom wall 3.

An upper opening section 13.2, which is arranged in the cover wall 4, widens towards the front side wall 10.

A hollow cylindrical tubular section 14 (call "flask neck" in the following) is securely connected to the edge of the opening 13. The flask neck 14 with the central axis $M_R$ thereof is inclined at an acute angle to the bottom wall 3. At the front end, the flask neck 14 projects upwards beyond the section of the cover wall 4, which is aligned parallel to the bottom wall 3.

The flask neck 14 has a circular cross-section. It has a first flask neck part 14.1, which has the shape of a hollow cylinder. The first flask neck part 14.1 is securely connected at a lower edge section 15.1 of a face side edge 15 to the edge of the lower opening section 13.1 (see FIGS. 3d and 3e).

Further, the flask neck 14 has a second flask neck part 14.2, which is a hollow cylinder segment. The second flask neck part 14.2 is connected at the side edges to the elliptical-shaped edge of the upper opening section 13.2. The second flask part at the face side edge thereof is connected to the upper edge section 15.2 of the first flask neck part 14.1, which projects upward beyond the front side wall 10.

Thus, the flask neck 14 penetrates both the upper region of the front side wall 10 as well as the front region of the cover wall 4. This is particularly advantageous with respect to removing cells from the growth area 12 using a pipette or a scraper. The invention is not limited to culture flasks with this advantageous special feature, rather can also be used with culture flasks in which the flask neck penetrates only a front side wall 10 and not the cover wall 4.

The flask neck 14 has an external thread 16 on the outer periphery for screwing on a screw cap. The external thread 16 advantageously has a single thread pitch. This circulates twice, for example, around the periphery of the flask neck 14. The thread is an acme screw thread, a V-thread, or flat thread, for example. The thread profile in the longitudinal section preferably has straight line thread flanks (see FIGS. 3a and 3d).

On both sides, the external thread 16 has vertical flattenings 17, 18 of the thread profile.

First projections in the shape of circular cylindrical pins 19, 20 project outwards, located on diametrically opposed sides of the flask neck. The pins 19, 20 are arranged on the flask neck 14, on the side of the external thread 16 facing away from the outer end of the flask neck 14. They are aligned horizontally and positioned precisely on the central plane of the flask neck 14. Due to the circular cylindrical shape thereof, the first projections are convex on the side of the external thread 16. The pins 19, 20, in a cylindrical circular area around the central axis of the flask neck 14, have a contour converging toward the external thread 16.

The flask neck 14 has a container opening 21 at the front end. Further, the flask neck has a circumferential, conical first sealing surface 22 on the front end on the inner periphery thereof. The first sealing surface 22 surrounds the container opening 21.

The walls 3 to 11 define a chamber 23 (also called "culture chamber 23").

The bottom wall 3 and the side walls 5 to 10 and the first flask neck part 14.1 belong to a flask lower part 24. The cover wall 4 and the second flask neck part 14.2 belong to a flask upper part 25.

The flask upper part at the edge is circumferentially connected to the upper edges of the side walls 5, 6, 7, 8, 9 and at the rear end of the first flask neck part 14.1. The connection is an ultrasonic weld connection, an infrared weld connection or an adhesive bond. With respect to the suitably constructed shape of the edges and performing the connections, reference is made to the patent applications EP 13 000 264.5 and U.S. 61/754,180, the content of which is hereby incorporated by reference into this application.

According to FIGS. 1d and 4a-4e, a screw cap 26 for closing the flask neck has a circular cap bottom 27 and a hollow cylindrical cap casing 28, connected to the edge of the cap bottom. The cap casing 28 borders a cap opening 29 opposite from the cap bottom 27. The cap casing 28 has a widening 30 there. Starting from the widening 30, axially-extending grip ribs 31 are arranged on the outside of the cap casing 29 that are uniformly distributed about the outer periphery 32 of the cap casing 28.

The screw cap 26 has an internal thread 34 on the inner periphery 33. This thread advantageously has a single thread pitch. The thread is an acme screw thread, a V-thread, or flat thread, for example. The thread profile in the longitudinal section preferably has straight line thread flanks. The thread profile, for example, circulates twice around the inner periphery 33 of the cap casing. The internal thread 34 is matched to the external thread 16, wherein a specific thread play exists between the internal thread and the external thread.

A stopper 35 in the shape of a bulge circulating around the central axis $M_s$ of the screw cap 26 projects backwards from the inside of the cap bottom 27. The stopper on the outer periphery has a second sealing surface 36 which is formed to seal at the first sealing surface 22 of the flask neck 14.

In the region of the widening 30, the cap portion has in the longitudinal section a step-shaped face surface 37. There, the cap casing 28 at the inner periphery 33 is provided with second projections 38, 39 in diametrically opposed peripheral positions.

The second projections 38, 39 project from the lower step of the step-shaped face surface 37 in the axial direction of the screw cap 26. They do not project to the rear beyond the widening 30. The second projections 38, 39 are hump-shaped. The second projections 38, 39 have a bulge in a circular cylindrical section surface circumferential about the central axis $M_s$ of the screw cap 26, that is directed backward away from the internal thread 34. The second projections 38, 39 each have a rounded latching groove 40 at the outer end.

The cap bottom 27, on the outside, has a marking 41.

The flask body 2 is preferably produced from polystyrene. The lower part of the flask 24 and the upper part of the flask 25 are injection molded separately and then subsequently connected together. The screw cap 26 is preferably integrally injection molded from polypropylene.

According to FIGS. 1a-1e, 2a-2d and 3a-3e, the screw cap 26 is screwed onto the flask neck 14. Due to the thread play, the screw cap 26 can be tilted slightly with respect to the flask neck 14. During screwing tightly, the first projections 19, 20 glide with their increasing shoulders over the increasing shoulders of the second projections 38, 39, until they latch in the latching groove 40. Here, the internal thread 34 with the front thread flank thereof is pressed against the rear thread flank of the external thread 16 (FIG. 1d). Due to that, the screw cap 26 can no longer be tilted with respect to the flask neck 14, but rather is held in a defined alignment. In this ventilation setting, the second sealing surface 36 does not yet lie against the first sealing surface 22, but rather a circumferential ventilation gap 42 is formed in between, having a specific ventilation cross-section (FIG. 1e). This is connected via the spiral-shaped ventilation channel 43, running circumferentially between the front flank of the external thread 16 and the rear flank of the internal thread 34, through the cap opening 29 to the surrounding area. Additionally, the ventilation gap 42 in the region of the flattenings 17, 18 of the external thread 16, is connected to the cap opening 29 and the surrounding area.

The ventilation setting is set for cultivating cells, tissues and microorganisms in the incubator. The ventilation setting is indicated to the user in that the marking 41 is located at 3 o'clock (FIG. 1a, b).

After cultivation, the user can close the screw cap 26 by further tightening the screw cap 26. The sealed setting is attained when the marking 41 is located at 5 o'clock (FIG. 2a). During tightly screwing, the decreasing shoulders of the second projections 38, 39 glide over the decreasing shoulders of the first projections 19, 20 until the second projections 38, 39 are released from the first projections 19, 20. As a result, the thread play is active again, until the second sealing surface 36 lies sealing on the first sealing surface 22. Due to the thread play, an exact alignment of the second sealing surface 36 on the first sealing surface 22 is supported, and thus a good seal (FIGS. 2c and 2d).

For opening the culture flask 1, the user unscrews the screw cap 26 in the opposite direction beyond the ventilation setting until the cap is separated from the flask neck.

With the following description of the example embodiments from FIGS. 5 to 8, the specifications "top" and "bottom" relate to a vertical alignment of the container with the bottom wall on the bottom and the at least one container opening on the top.

A roller bottle 44 and a spinner bottle 45 each have a hollow cylindrical container body 46, 47 with a planar bottom wall 48, 49 and at least one flask neck 14 on the upper end. The roller bottle 44 has only a single flask neck 14. The spinner bottle 45 has a central wide flask neck 14.1 and on the side thereof a further, less wide, flask neck 14.4, 14.5 inclined in different directions.

An Erlenmeyer flask 50 has a substantially conical container body 51 with a planar bottom wall 52 and a flask neck 14 on the upper end. The flask neck 14 of the culture containers 44, 45, 50, named above, are formed like the flask neck 14 of the culture flask 1 from FIGS. 1a-1e, 2a-2d and 3a-3e.

A test tube 53 has a slender cylindrical container body 54 with a conical bottom wall 55 and a tubular section 14 with external thread 16 at the upper end. The tubular section 14 is formed corresponding to the flask neck of the culture flask 1 described above.

The flask necks 14, or respectively the tubular section 14 can be closed using screw caps 26, or respectively 26.1, 26.2, 26.3, which are formed according to the screw cap 26 of the culture flask 1 described above.

The culture containers from FIGS. 5a-d, 6a-6d, 7a-7d and 8a-8d can be ventilated using the setting of the screw caps 26, or respectively 26.1, 26.2, 26.3 in the ventilation setting and are sealed by tightly screwing the screw cap. They can be used advantageously for cultivating samples.

This completes the description of the preferred and alternate embodiments of the invention. Those skilled in the art may recognize other equivalents to the specific embodiment described herein which equivalents are intended to be encompassed by the claims attached hereto.

LIST OF REFERENCE NUMBERS 1 culture container (culture flask)
2 container body (flask body)
3 bottom wall
4 cover wall
4.1 rectangular section
4.2 trapezoidal section
5-10 side walls
11 sloped wall
12 growth area
13 opening
13.1 lower opening section
13.2 upper opening section
14, 14.3-14.5 tubular section (flask neck)
14.1 first flask neck part
14.2 second flask neck part
15 face side edge
15.1 bottom edge section
15.2 top edge section
16, 16.1-16.3 external thread
17, 18 flattening
19, 19.1-19.3 first projections (pins)
20, 20.1-20.3
21 container opening
22 first sealing surface
23 chamber (culture chamber)
24 flask lower part
25 flask upper part
26 screw cap
27 cap bottom
28 cap casing
29 cap opening
30 widening
31 grip rib
32 outer periphery
33 inner periphery
34 internal thread
35 stopper
36 second sealing surface
37 face surface
38, 39 second projection
40 latching groove
41 marking
42 ventilation gap
43 ventilation channel
44 roller bottle
45 spinner bottle
46, 47 container body
48, 49 bottom wall
50 Erlenmeyer flask
51 container body
52 bottom wall
53 test tube
54 container body
55 bottom wall

The invention claimed is:

1. A screw cap lidded container for laboratory use comprising:

a container body (2) defining a chamber (23),
a tubular section (14) of the container body (2) that is connected at the rear to the chamber (23) and has a container opening (21) in the front,
an external thread (16) on the outer periphery of the tubular section (14),
a circumferential first sealing surface (22) on the tubular section (14),
at least one first projection (19, 20), which projects from the container body (2) at a peripheral position of the tubular section (14),
a screw cap (26),
an internal thread (34) on the inner periphery (33) of the screw cap (26) that can be screwed onto the external thread (16) with thread play,
a circumferential second sealing surface (36) on the screw cap (26), that by screwing the screw cap (26) tightly onto the tubular section (14) can be brought into sealing contact with the first sealing surface (22), and
at least one second projection (38, 39), which projects from the screw cap (26) at a peripheral position of the screw cap (26),
wherein the first projection (19, 20) on a front side, in a circular cylindrical cut surface about a central axis of the tubular section (14) has an increasing shoulder towards the external thread (16), and/or the second projection (38, 39) on a back side in a circular cylindrical cut surface about a central axis of the screw cap (26) has an increasing shoulder towards opening (19), wherein when screwing the screw cap (26) tightly onto the tubular section (14), the first and second projections (19, 20; 38, 39) come into contact and glide onto each other with the at least one increasing shoulder, whereby a forward directed axial force towards the opening of the neck is exerted on the screw cap (26), whereby due to the play between the internal and external thread the internal thread (34) is pressed with a flank against a thread flank of the external thread (16), and an axial displacement of a screw cap (26) takes place which results in a ventilation gap between the sealing surfaces (22, 36), the first and second projections are moved past each other during further screwing tightly and the first and second sealing surfaces (22, 36) attain a sealed setting in which they lie sealed against each other.

2. The screw cap lidded container according to claim 1, in which the tubular section (14) has the first sealing surface (22) on the inner periphery of the tubular section (14) and the screw cap (26) has the second sealing surface (36) on a stopper (35) projecting from the cap bottom (27).

3. The screw cap lidded container according to claim 1, in which the at least one first projection (19, 20) on the front side, in the circular cylindrical cut surface about the central axis of the tubular section (14), has a decreasing shoulder, and/or the at least one second projection (38, 39) on the back side, in a circular cylindrical cut surface about the central axis of the screw cap (26), has a decreasing shoulder, such that during further screwing the screw cap (26) tightly from the ventilation position into the sealed position, the first and second projections glide over each other with the at least one decreasing shoulder, whereby the forward directed force exerted on the screw cap (26) is completely or partially absorbed until the sealed setting is attained.

4. The screw cap lidded container according to claim 1, in which the container body (2) has a plurality of first projections (19, 20) distributed uniformly about the tubular section, and the screw cap (26) has a corresponding number of second projections (38, 39) distributed uniformly about the cap opening (29).

5. The screw cap lidded container according to claim 4, in which the container body (2) has two first projections (19, 20) arranged on diametrically opposed sides of the tubular section (14), and the screw cap (26) has two second projections (38, 39) arranged on diametrically opposed sides of the cap opening (29).

6. The screw cap lidded container according to claim 1, in which the at least one first projection (19, 20) is convex on the front side, and/or in which the at least one second projection (38, 39) is convex on the back side.

7. The screw cap lidded container according to claim 1, in which the at least one first projection (19, 20) projects outward from the tubular section (14) behind the external thread (16), and/or in which the at least one second projection projects from the cap casing (28) behind the internal thread (34).

8. The screw cap lidded container according to claim 1, in which the at least one first projection (19, 20) is a circular cylindrical pin projecting radially from the tubular section (14) behind the external thread (16), and/or in which the at least one second projection (38, 39) is a hump projecting from the cap casing behind the internal thread (34).

9. The screw cap lidded container according to claim 1, in which the at least one second projection (38, 39) on an outer end has a latching groove (40) into which the at least one first projection (19, 20) latches in the ventilation position, or in which the at least one first projection (19, 20) on the outer end has a latching groove (40) into which the at least one second projection (38, 39) latches in the ventilation position.

10. The screw cap lidded container according to claim 9, in which the latching groove (40) is rounded.

11. The screw cap lidded container according to claim 1, in which the at least one second projection (38, 39) projects inward from the cap casing (28).

12. The screw cap lidded container according to claim 1, in which the screw cap (26) has a radial widening (30) on the outer edge of the cap casing (28) thereof, and the at least one second projection (38, 39) is arranged within the widening (30).

13. The screw cap lidded container according to claim 1, in which the external thread (16) and/or the internal thread (34) have at least one flattening (17, 18) of the thread profile.

14. The screw cap lidded container according to claim 1, in which the screw cap (26) has a marking (41) on the outside.

15. The screw cap lidded container according to claim 1, that is a culture flask (1), or a test tube (53), or a roller bottle (44), or a spinner bottle (45), or an Erlenmeyer flask (50), or a laboratory bottle.

16. The screw cap lidded container according to claim 1, whose container body (2) is produced from polystyrene or polycarbonate or from another plastic and/or whose screw cap (26) is produced from polypropylene or polyethylene or polytetrafluoroethylene or from another plastic or from a combination of the named materials.

* * * * *